(12) United States Patent
Valet et al.

(10) Patent No.: US 11,786,263 B2
(45) Date of Patent: Oct. 17, 2023

(54) SOUND WAVE TREATMENT DEVICE

(71) Applicant: Richard Wolf GmbH, Knittlingen (DE)

(72) Inventors: Dominic Valet, Kraichtal (DE);
Alexander Wössner, Kraichtal (DE)

(73) Assignee: RICHARD WOLF GMBH, Knittlingen (DE)

( * ) Notice: Subject to any disclaimer, the term of this patent is extended or adjusted under 35 U.S.C. 154(b) by 1370 days.

(21) Appl. No.: 16/026,128

(22) Filed: Jul. 3, 2018

(65) Prior Publication Data
US 2019/0008535 A1  Jan. 10, 2019

(30) Foreign Application Priority Data

Jul. 4, 2017 (DE) .......................... 102017211400.2

(51) Int. Cl.
| | |
|---|---|
| *H01F 27/32* | (2006.01) |
| *H01F 27/00* | (2006.01) |
| *H01F 27/30* | (2006.01) |
| *H01F 27/38* | (2006.01) |
| *H02M 1/00* | (2006.01) |

(Continued)

(52) U.S. Cl.
CPC .......... *A61B 17/225* (2013.01); *B06B 1/0207* (2013.01); *G10K 15/043* (2013.01);
(Continued)

(58) Field of Classification Search
CPC ....... B06B 1/0207; G10K 15/043; H01F 5/02; H01F 27/306; H01F 27/325;
(Continued)

(56) References Cited

U.S. PATENT DOCUMENTS 1,837,413 A * 12/1931 Dobson ............... H01F 27/2823
336/208
5,673,013 A *  9/1997 Moody ..................... H01F 5/02
336/208

(Continued)

FOREIGN PATENT DOCUMENTS

CN         105208707 A  * 12/2015
CN         205080987 U  *  3/2016
(Continued)

OTHER PUBLICATIONS

Search Report dated Jul. 4, 2017 in DE Application No. 10 2017 211 400.2.

*Primary Examiner* — Shawki S Ismail
*Assistant Examiner* — Joselito S. Baisa
(74) *Attorney, Agent, or Firm* — Panitch Schwarze Belisario & Nadel LLP

(57) ABSTRACT

A sound wave treatment device for medical treatment using compression waves, in particular for lithotripsy, includes a sound wave generator, a plurality of piezo elements that are coupled to the sound wave generator, and, an electrical high voltage unit that is set up for supplying the piezo elements with high electrical voltage. The high voltage unit has a blocking converter unit having a transformer, wherein the transformer has a primary coil, a high voltage coil, and spacers, wherein the high voltage coil has a plurality of high voltage windings that are embedded in an insulating mass and are positioned using the spacers such that adjacent high voltage windings are at a defined distance (a) from one another due to the spacers.

12 Claims, 3 Drawing Sheets

(51) Int. Cl.
*G10K 15/04* (2006.01)
*A61B 17/225* (2006.01)
*H01F 27/40* (2006.01)
*B06B 1/02* (2006.01)
*H01F 5/02* (2006.01)
*H03K 3/57* (2006.01)
*H01F 38/42* (2006.01)
*A61B 17/00* (2006.01)
*H02M 3/335* (2006.01)

(52) U.S. Cl.
CPC ............ H01F 5/02 (2013.01); H01F 27/006 (2013.01); H01F 27/306 (2013.01); H01F 27/325 (2013.01); H01F 27/402 (2013.01); H02M 1/00 (2013.01); *A61B 2017/00017* (2013.01); *H01F 27/327* (2013.01); *H01F 27/38* (2013.01); *H01F 2005/022* (2013.01); *H01F 2005/025* (2013.01); *H01F 2038/426* (2013.01); *H02M 3/33523* (2013.01); *H03K 3/57* (2013.01)

(58) Field of Classification Search
CPC ........... H01F 27/2738; H01F 2005/025; H01F 2005/022; H01F 27/327; H02M 1/00; H02M 3/33523
USPC .......................................... 310/318
See application file for complete search history.

(56) References Cited

U.S. PATENT DOCUMENTS

| | | | |
|---|---|---|---|
| 6,433,663 B1 * | 8/2002 | Fitzgerald, Jr. ......... | H01F 38/42 336/198 |
| 8,390,416 B2 * | 3/2013 | Leijssen .................... | H01F 5/00 336/195 |
| 8,979,776 B2 * | 3/2015 | Gelbart ................ | A61B 17/225 601/4 |
| 2007/0057749 A1 * | 3/2007 | Yanagisawa .......... | H02M 1/126 333/185 |
| 2008/0191815 A1 * | 8/2008 | Yanagisawa .......... | H02M 1/126 333/204 |
| 2010/0214049 A1 * | 8/2010 | Park ...................... | H01F 27/325 336/170 |
| 2011/0050379 A1 * | 3/2011 | Kim ...................... | H01F 27/306 336/200 |
| 2012/0103731 A1 * | 5/2012 | Sakuma .................... | H01F 5/02 187/292 |
| 2017/0331383 A1 * | 11/2017 | Hsiao ...................... | H02M 3/01 |

FOREIGN PATENT DOCUMENTS

| | | | | |
|---|---|---|---|---|
| CN | 105943119 A | * | 9/2016 | |
| CN | 206589171 U | * | 10/2017 | |
| CN | 208589332 U | * | 3/2019 | |
| CN | 109300662 B | * | 12/2020 | ............ H01F 27/25 |
| DE | 4433224 C1 | | 3/1996 | |
| DE | 102010055836 B4 | | 3/2013 | |
| DE | 102015208774 A1 | * | 12/2016 | ......... H05B 33/0815 |
| DE | 102020114516 A1 | * | 12/2021 | ............ H01F 27/24 |
| EP | 0918342 A1 | | 5/1999 | |
| EP | 1163884 A1 | | 12/2001 | |
| JP | H0595021 U | * | 5/1992 | |
| JP | H0536813 U | * | 5/1993 | |
| JP | H0797880 A | * | 4/1995 | |
| JP | 2009054937 A | * | 3/2009 | |
| JP | 2011176141 A | * | 9/2011 | |
| JP | 2013016695 A | * | 1/2013 | |
| WO | WO-2011021288 A1 | * | 2/2011 | ............ B66B 7/044 |

* cited by examiner

SOUND WAVE TREATMENT DEVICE

CROSS-REFERENCE TO RELATED APPLICATIONS

This application claims priority under 35 U.S.C. § 119(b) to German Application No. 10 2017 211 400.2, filed Jul. 4, 2017, the disclosure of which is incorporated herein by reference in its entirety.

BACKGROUND OF THE INVENTION

This disclosure relates to a sound wave treatment device for medical treatment using compression waves, in particular for lithotripsy.

Sound wave treatment devices are currently widely used in medicine, and not just for shock wave therapy for fragmenting stones (lithotripsy), but also for numerous other applications, such as, for example, for non-invasive treatment of the soft tissue region located near the bone or for treating large surface areas for, for example, muscle spasms, muscle cramps, thickening of the connective tissue, or even for treating soft tissue regions such as fat and skin tissue, cellulitis, chronic wounds, centers of inflammation, and the like.

During extracorporeal sound wave lithotripsy (ESWL), sound waves are generated by spherically arranged piezo elements concertedly excited with high voltage via discharge capacitors and thyristor switches, wherein the sound waves overlay one another in a focus zone at a locally very high pressure (sometimes more than 100 MPa). The focus zone is targeted, for example, on a urinary or kidney stone disposed in the body of a patient so that the stone is blasted apart by the pressure. For example, DE 10 2010 055 836 B4 describes such a piezoelectric shock wave source, which may be controlled as described in DE 44 33 224 C1.

There are stringent safety requirements for protecting patients and operators, since such ESWL devices work with high voltage. According to the third edition of international standard IEC 60601-1, which considers alternating current voltage greater than 1 kV and direct current voltages greater than 1.5 kV to be high voltage, two independent means of patient protection (MOPP) are required for parts of medical devices that come into contact with patients. Two independent means of operator protection (MOOP) are required for parts of devices that come into contact with the operator, but not with the patient. In addition, first failure safety is required, which means that neither the patient nor the operator is exposed to a hazard when a failure occurs for the first time.

High insulation strength and first failure safety must be maintained, therefore, if the installation space provided for supplying the high voltage in such for ESWL device is reduced.

The sound wave treatment device according to claim 1 of the present disclosure has a high insulation strength and provides first failure safety while having a small insulation space. Advantageous embodiments of the sound wave treatment device disclosed herein may be found in the subordinate claims, in the description below, and in the drawings.

BRIEF SUMMARY OF THE INVENTION

The sound wave treatment device disclosed herein for medical treatment with compression waves, in particular for lithotripsy, has a sound wave generator, a plurality of piezo elements that are coupled to the sound wave generator, and an electrical high voltage unit for supplying the piezo elements with high electrical voltage. The high voltage unit has a blocking converter unit having a transformer. The transformer has a primary coil, a high voltage coil, and spacers. The high voltage coil has a plurality of high voltage windings that are embedded in an insulating mass, preferably essentially free of air bubbles, and are positioned using the spacers such that adjacent high voltage windings are at a defined distance from one another due to the spacers.

The blocking converter unit in the high voltage unit has the advantage that the high voltage side of the transformer (secondary side) is galvanically separated from the input voltage side of the transformer (primary side), enhancing first failure safety. Embedding in an insulating mass, preferably essentially free of air bubbles, in conjunction with the spacers, increases the insulation strength while allowing a smaller installation space for the transformer. Simulations and tests have demonstrated that the sound wave treatment device disclosed herein also has shorter charging times for the discharge capacitors so that the sound wave treatment device may be used more efficiently.

Optionally, the high voltage coil may be wound on a high voltage coil former and the spacers may project radially out of the high voltage coil former between adjacent high voltage windings. The maximum field strengths occurring between adjacent high voltage windings are reduced by the spacers projecting therebetween, so that the transformer has greater insulation strength.

Optionally, the high voltage coil may be wound on a high voltage coil former, and the high voltage windings may run in a groove running on an outer curved surface area of the high voltage coil former. This makes it particularly simple to provide the spacers, since they may be formed by the high voltage coil former itself.

Optionally, the spacers and/or the groove may have centering surfaces that urge the high voltage windings into a specific position. Since the insulating mass may be cast as a casting compound, for example, over the high voltage windings, the centering surfaces ensure precise spacing of adjacent high voltage windings that does not change during casting. In addition, air bubble inclusions are avoided during casting due to the defined spacing. That is, undesired air bubbles in the insulating mass could permit local field strengths that are too high, which has a negative effect on insulation strength. The centering surfaces may be formed, for example, using the oblique leg surfaces of a V-shaped or U-shaped groove.

Optionally, the high voltage coil may be wound on a high voltage coil former and the spacers may be a thread on the high voltage coil former. The thread may define a helical groove running around the high voltage coil former, wherein the thread lands between the groove form the spacers. Providing spacers in the form of a thread on the high voltage coil former is little complex and permits the transformer to have a small installation size.

Optionally, the transformer may have a first curved surface area having a first radius and a second curved surface area having a second radius, wherein the primary coil is wound on the first curved surface area and the high voltage coil is wound on the second curved surface area, wherein the first radius is different, preferably smaller, than the second radius. Due to the curved surface areas having a different radius, magnetic couplings, and resultant mechanical tensions, between the primary coil and the high voltage coil are reduced.

Optionally, the primary coil may run, at least in part, within the high voltage coil. In addition, the high voltage coil may optionally be wound on a high voltage coil former and the primary coil on a primary coil former, wherein the high voltage coil former may coaxially surround the primary coil former. Thus, it is particularly simple to assemble the transformer and later to cast the insulating mass around the high voltage coil.

Optionally, the transformer may have a first auxiliary coil for indirectly measuring the high voltage on the output side. The auxiliary coil may be used, galvanically separated from the high voltage, for measuring the high voltage, so that the latter may be regulated, or, if there is a fault, so that it may be displayed as an alarm or turned off. Thus, the auxiliary coil contributes to first failure safety without introducing another fault source via a galvanic coupling with high voltage.

Optionally, the transformer may have a second auxiliary coil that is for redundant indirect measurement of the high voltage on the output side and that is arranged and switched parallel to the first auxiliary coil. If the high voltage measurement via the first auxiliary coil fails, the second auxiliary coil can increase the first failure safety. Measurements via the parallel auxiliary coils may also be compared to one another and, if there are discrepancies, an error may be displayed or maintenance may be triggered.

Optionally, the first auxiliary coil and/or the second auxiliary coil may be arranged on a ground end face, connected to a ground, of the transformer. This has the advantage that the first and/or the second auxiliary coil consume less energy stored in in the magnetic field of the transformer as current, which energy is then not available from the high voltage coil for charging the discharge capacitors.

Optionally, the primary coil and the first auxiliary coil and/or the second auxiliary coil may be wound on a primary coil former. Thus, providing the first auxiliary coil and/or second auxiliary coil is particularly simple when assembling the transformer.

Optionally, the spacers may have a material with a relative permittivity of greater than 3.0 at a frequency of 1.0 kHz and a temperature of 23° C. Simulations and tests have demonstrated that the maximum occurring field strengths in this range of permittivity of the spacers are below the allowed maximums, e.g. 20 kV/mm, for the required insulation strength.

Optionally, the insulating mass may have a material having a relative permittivity of greater than 4.0 at a frequency of 1.0 kHz and a temperature of 23° C. Simulations and tests have demonstrated that the maximum occurring field strengths in this range of permittivity of the insulating mass are below the allowed maximums, e.g. 30 kV/mm, for the required insulation strength.

Optionally, the transformer may have a ferrite core having a saturation flux density of at least 200 mT. This ensures efficient energy transfer from the primary coil to the high voltage coil. The ferrite core may be produced from fine-grained pulverized metal oxides.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
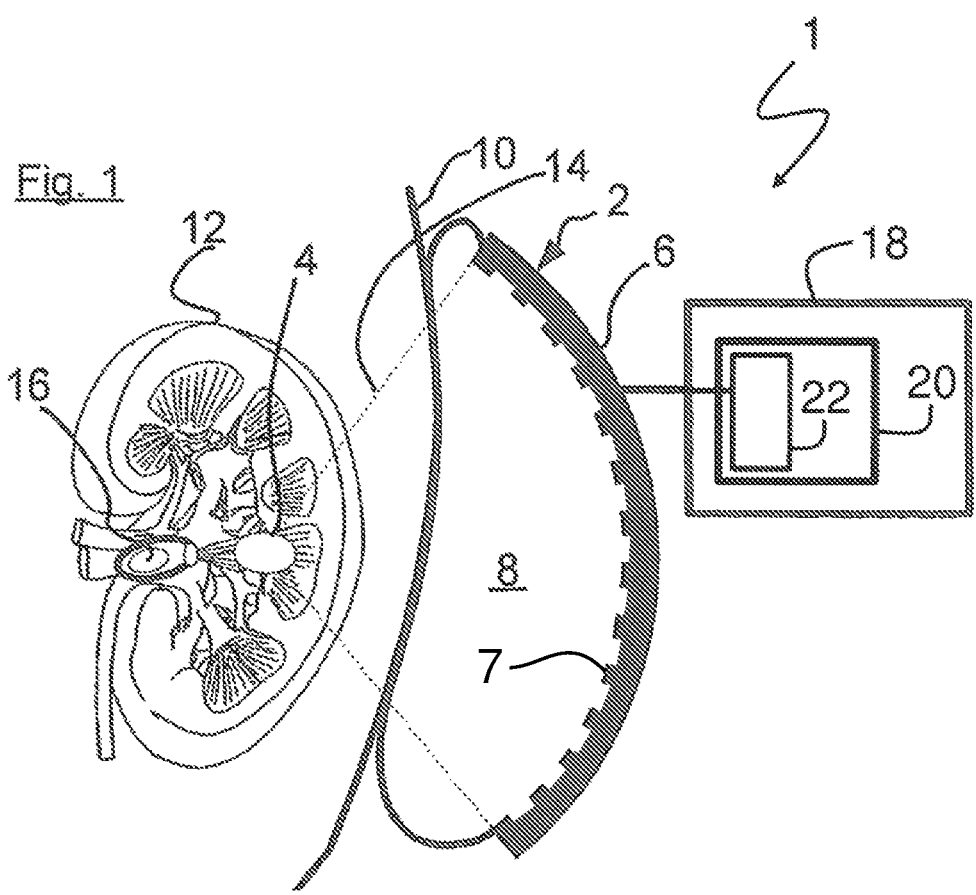
FIG. 1 is an exemplary embodiment of the sound wave treatment device described herein.

Theسsound wave treatment device 1 depicted in FIG. 1 is an apparatus for shockwave lithotripsy. This apparatus has a therapy field source in the form of a sound wave generator 2. The sound wave generator 2 fragments a kidney stone 4, or may be used for fragmenting other body stones, such as, for example, bladder and urinary stones in the urinary tract.

The sound wave generator 2 has a carrier calotte 6 having a plurality of piezo elements 7 attached thereto and having a soft elastic coupling bellows 8 connecting to the distal side of the carrier calotte 6. When therapy begins, the coupling bellows 8 of the sound wave generator 2 is positioned against the exterior of the patient's body 10 in a region adjacent to the kidney 12. Then it must be assured that the position of the focus of a focused acoustic shock wave field 14 emitted by the sound wave generator 2 coincides with the position of the kidney stone 4 to be fragmented in order to introduce the energy of the shock wave field 14 only into the kidney stone 4 and not into the surrounding tissue.

An apparatus for imaging the treatment area, in this case the kidney stone 4, may be provided for precisely orienting the focus of the shock wave field 14 on the kidney stone 4. This apparatus is arranged in a capsule endoscope 16 that is used intracorporeally in the kidney 12.

However, it is also possible to obtain imaging of the treatment area extracorporeally (not shown), such as, for example, using suitable and precise ultrasound sonography, X-ray or computer tomography (CT), magnetic resonance tomography (MRT), positron emissions tomography (PET), or combinations thereof. For example, an ultrasound probe may be arranged in the coupling bellows 8 and oriented to the patient and the patient may be X-rayed, by means of an X-ray C arc, in an axis that includes an angle with the axis of the ultrasound probe. Thus, it would then be possible to determine of the position of the kidney stone 4 extracorporeally.

The sound wave generator 2 is connected to a control unit 18 that has an electrical high voltage unit 20, the latter itself having a blocking converter unit 22. The high voltage unit 20 is set up to supply high electrical voltage to the piezo elements 7 coupled to the sound wave generator 2. This is accomplished using discharge capacitors (not shown) that are charged by or in the high voltage unit 20 and are then discharged concertedly, for instance by means of thyristor switches, via the piezo elements 7. The piezo elements 7 convert the electrical energy obtained in this manner, at least in part, into kinetic energy or deformation energy and thus generate the shock wave field 14 in the sound wave generator 2. The discharge capacitors are charged via the blocking converter unit 22 as described in greater detail in FIG. 2.

Figure 2:
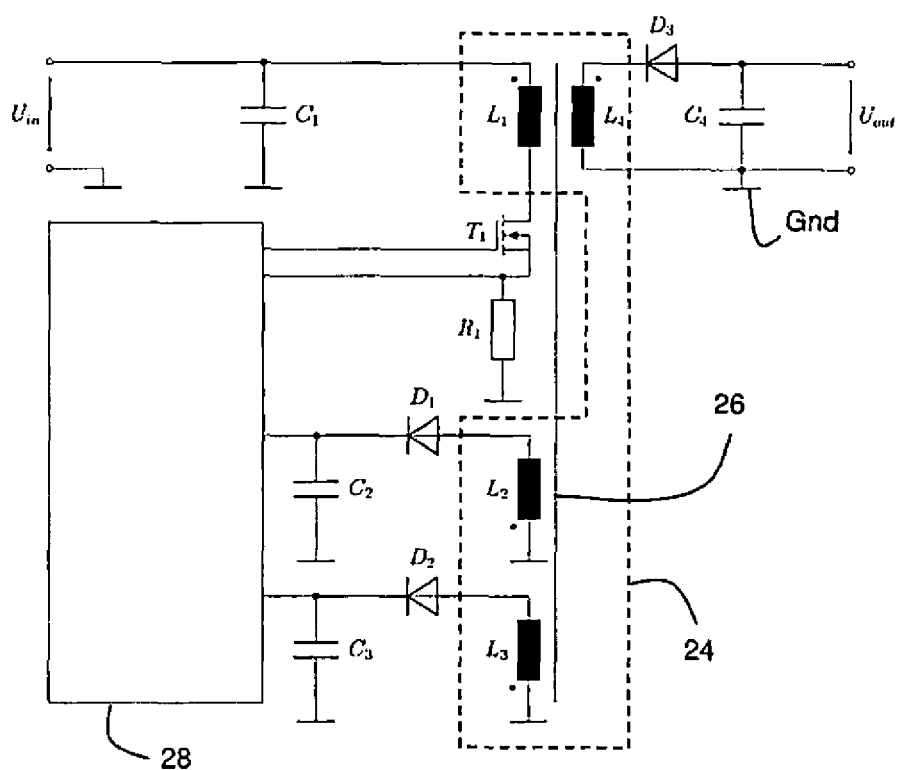
FIG. 2 is a circuit diagram of an exemplary embodiment of the high voltage unit of the sound wave treatment device described herein.

The circuit diagram in FIG. 2 illustrates schematically how the blocking converter unit 22 is wired. The blocking converter unit 22 has a transformer 24 with an input-side primary coil $L_1$, a first auxiliary coil $L_2$, a second auxiliary coil $L_3$, and an output-side high voltage coil $L_4$, wherein the coils have a common ferrite core 26. The functioning of the transformer 24 is measured, regulated, and monitored via a measuring, regulating, and monitoring unit 28 that may be part of the high voltage unit 20 or part of the control unit 18. The measuring, regulating, and monitoring unit 28 may switch a transistor $T_1$ in a conductive manner and supply current to the primary coil $L_1$ by means of an input voltage $U_{in}$ until a maximum current, adjustable via a resistor $R_1$, is attained. As long as the transistor $T_1$ is conductive, a diode $D_3$ connected on the output side to the high voltage coil $L_4$ blocks a flow of current in the high voltage coil $L_4$. Likewise, diodes $D_1$ and $D_2$, respectively, block currents through the first auxiliary coil $L_2$ and the second auxiliary coil $L_3$, respectively. The coils have respective capacities $C_1$, $C_2$, $C_3$, and $C_4$, which must be taken into account when the transformer is dimensioned and designed. The first auxiliary coil $L_2$ and the second auxiliary coil $L_3$ are preferably embodied not as wire coils, but instead as foil coils parallel to one another. This demonstrated greater regulating accuracy in tests.

The blocking converter unit 22 thus stores energy in the magnetic field during a conducting phase of the transistor $T_1$ using a current through the primary coil $L_1$. As soon as the transistor $T_1$ interrupts the current through the primary coil $L_1$ (blocking phase), the energy stored in the magnetic field leads to a current in the output-side high voltage coil $L_4$ in the first auxiliary coil $L_2$, and in the second auxiliary coil $L_3$, in the forward direction of the diodes $D_4$, $D_2$, and $D_3$, respectively. The current in the output-side high voltage coil $L_4$ builds an output-side high voltage $U_{out}$ for charging discharge capacitors (not shown), wherein the output-side high voltage $U_{out}$ may be measured independent of one another by means of the first auxiliary coil $L_2$ and the second auxiliary coil $L_3$ in the measuring, regulating, and monitoring unit 28. The first auxiliary coil $L_2$ and the second auxiliary coil $L_3$ are advantageously arranged on an output side of the transformer 24 connected to a ground Gnd.

The measuring, regulating, and monitoring unit 28 switches the transistor $T_1$ cyclically (at greater than 20 kHz to 10 MHz, that is, above the audible range to avoid static noise and easily simulated) between conductive phase and blocked phase, so that the discharge capacitors may be charged in about 100 ms to 200 ms to a high voltage of, for example, 8.9 kV in about 5,000 to 2,000,000 cycles. The energy that is transmitted from the primary coil $L_1$ to the high voltage coil $L_4$ per cycle is buffered in the magnetic field, preferably in an air gap of the ferrite core 26. The high voltage coil $L_4$ is thus galvanically separated from the measuring, regulating, and monitoring unit 28, which contributes to first failure safety.

Simulations and practical tests have demonstrated that, after a high voltage pulse of about 5 μs, the transformer 24 needs approx. 5 μs for reducing residual magnetization and residual charge, so that a maximum pulse control factor $v_T$=0.5 results. When using a ferrite core having, for example, a saturation flux density $B_{sat}$=350 mT and a magnetic active surface of A=209 mm², with a primary coil $L_1$ of N=5 windings and a cycle frequency of 50 kHz, the following AC input voltage $U_{in}$ results:

$$U_{in} = \frac{N \cdot B_{sat} \cdot A \cdot f}{\partial_T} = \frac{5 \cdot 0.35 \text{ T} \cdot 209 \cdot 10^{-6} \text{ m}^2 \cdot 50 \cdot 10^3 \text{ s}^{-1}}{0.5} = 36.58 \text{ V}$$

If the high voltage coil $L_4$ has 85 to 100 windings, e.g., 95 windings, that is, the transformer 24 has a winding ratio of approx. 18 to 19, for example, a high voltage of 8.9 kV may be built up on the discharge capacitors in approx. 150 ms.

Figure 3A:
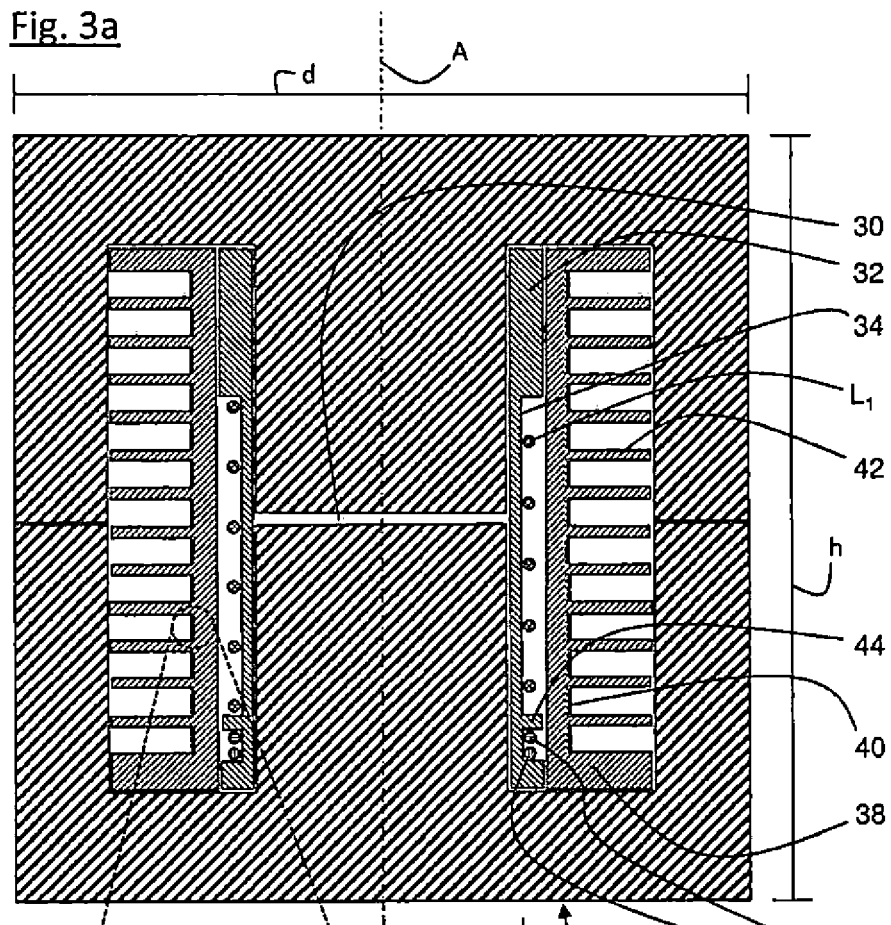
FIG. 3a is a cross-section of an exemplary embodiment of the transformer of the high voltage unit of the sound wave treatment device disclosed herein.

FIG. 3a depicts the geometrical structure of the transformer 24 in cross-section having a longitudinal axis A. Given the exemplary parameters described herein, the transformer 24 may be embodied with a diameter d of less than 50 mm and with a height h of less than 50 mm. The ferrite core 26 is embodied in two parts, wherein the two parts enclose an air gap 30 that is 0.3 mm to 1.5 mm wide, preferably 1 mm wide. The ferrite core 26 may be, for example, a core in the form of the ETD49/25/16 by EPCOS®, with a so-called N87 ferrite on MnZn base.

Disposed in the ferrite core 26 is an inner primary coil former 32 that defines a first outer curved surface area 34 having a first radius $R_1$. The primary coil $L_1$ is wound on the first curved surface area 34 with five windings. The primary winding $L_1$ preferably does not comprise one wire that is wound around the curved surface area 34 five times, but instead comprises five wires that are switched parallel to one another and that are each wound around the curved surface area 34 one time. With high frequencies, this is an advantage in particular when the current does not flow evenly through the wire cross-section due to the skin effect, but instead flows more strongly on the outer surface of the wire. Placed over the inner primary coil former 32 is a high voltage coil former 38 that defines a second outer curved surface area 40 having a second radius $R_2$ that is larger than the first radius $R_1$. The second radius $R_2$ is preferably approx. 1 mm to 3 mm larger than the first radius $R_1$, for example 1.5 mm. The high voltage coil $L_4$ is wound, with 91 windings, on the second curved surface area 40. The high voltage coil former 38 has 12 high voltage coil lands 42 that define 13 sections of the high voltage coil $L_4$, each section having 7 windings. The primary coil $L_1$ is thus disposed completely inside of the high voltage coil $L_4$, wherein the high voltage coil former 38 coaxially surrounds the primary coil former 32.

The first auxiliary coil $L_2$ and the second auxiliary coil $L_3$ are wound on the primary coil former 32 at a ground end face 36 of the transformer 24 and are kept spaced apart and insulated from the primary coil $L_1$ by means of a primary coil bar 44. The primary coil $L_1$ and the high voltage coil $L_4$ are preferably connected to ground Gnd at the ground end face 36 where the first auxiliary coil $L_2$ and the second auxiliary coil $L_3$ are disposed. Since the current in the primary coil $L_1$ may be greater than 20 A, a wire diameter of 0.5 mm or greater is advantageous for the five parallel wires of the primary coil $L_1$.

Figure 3B:
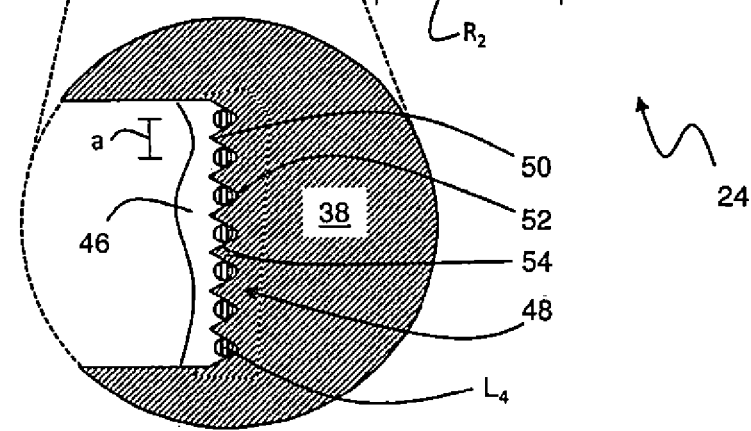
FIG. 3b is a detail section of the cross-section of an exemplary embodiment of the transformer of the high voltage unit of the sound wave treatment device disclosed herein.

As may be seen in the detail view in FIG. 3b, the high voltage coil $L_4$ is embedded, essentially free of air bubbles, in an insulating mass 46, wherein the insulating mass 46 was preferably cast over the high voltage coil $L_4$ under a vacuum seal and hardened. The 7 high voltage windings per section of the high voltage coil $L_4$ are wound on a fine thread of the second outer curved surface area 40, wherein the fine thread functions as spacers 48. Adjacent high voltage windings within a section of the high voltage coil $L_4$ thus are spaced from one another at a precisely defined distance a. Thread lands 50 project radially from the high voltage coil former 38 between adjacent high voltage windings that are disposed in a V-shaped thread groove 52 on the second outer curved surface area 40. The thread lands 50 and the V-shaped thread groove 52 define centering surfaces 54 that urge the high voltage windings into a specific position. The entire circumference of each high voltage winding is preferably embedded in the thread groove 52 and the thread lands 50 project beyond the wire diameter of the high voltage coil $L_4$ between adjacent high voltage windings.

The high voltage coil former 38 and thus, in this embodiment, the spacers 48, as well, are preferably made from TECAPEEK®, which has a relative permittivity of 3.3 at a frequency of 1.0 kHz and a temperature of 23° C. The insulating mass may be WEVO® PU 552 FL with a hardness of 300 in a 5:1 mixing ratio, for example, which has a relative permittivity of 4.6 at a frequency of 1.0 kHz and a temperature of 23° C., so that insulating security is assured up to a maximum field strength of 29 kV/mm.

The sound wave treatment device disclosed herein may be operated highly insulating and first fault safe with a high voltage transformer 24 that may be embodied with a diameter d of less than 50 mm and with a height h of less than 50 mm and that weighs less than 0.5 kg. In addition, the high voltage transformer 24 described herein ensures power of at least 70 W with more than 80% efficiency.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A sound wave treatment device (1) for medical treatment using compression waves, in particular for lithotripsy, having:
 a sound wave generator (2),
 a plurality of piezo elements (7) that are coupled to the sound wave generator (2), and,
 an electrical high voltage unit (20) that is set up for supplying the piezo elements (7) with high electrical voltage
 wherein
  the high voltage unit (20) has a blocking converter unit (22) having a transformer (24), wherein the transformer (24) has a primary coil ($L_1$), a high voltage coil ($L_4$), and spacers (48), wherein the high voltage coil ($L_4$) has a plurality of high voltage windings that are embedded in an insulating mass (46) and are positioned using the spacers (48) such that adjacent high voltage windings are at a defined distance (a) from one another due to the spacers (48), wherein the high voltage coil ($L_4$) is wound on a high voltage coil former (38) and the spacers (48) are a thread on the high voltage coil former (38), wherein an entire circumference of each high voltage winding is embedded in a V-shaped groove (52) of the thread, each V-shaped groove (52) has centering surfaces (54) that urge the respective winding into a specific position, and wherein lands (50) of the thread project beyond a wire diameter of the high voltage coil ($L_4$) between adjacent high voltage windings, wherein the transformer (24) has a first auxiliary coil ($L_2$) for indirectly measuring the output-side high voltage, wherein the transformer (24) has a second auxiliary coil ($L_3$) that is for redundant indirect measurement of the output-side high voltage and that is arranged parallel to the first auxiliary coil ($L_2$), and wherein the first auxiliary coil ($L_2$) and the second auxiliary coil ($L_3$) are embodied as foil coils parallel to one another.

2. The sound wave treatment device according to claim 1, wherein the high voltage windings are embedded in the insulating mass (46) essentially free of air bubbles.

3. The sound wave treatment device according to claim 1, wherein the transformer (24) has a first curved surface area (34) having a first radius ($R_1$) and a second curved surface area (40) having a second radius ($R_2$), wherein the primary coil ($L_1$) is wound on the first curved surface area (34) and the high voltage coil ($L_4$) is wound on the second curved surface area (40), wherein the first radius ($R_1$) is different than the second radius ($R_2$).

4. The sound wave treatment device according to claim 1, wherein the primary coil ($L_1$) runs, at least in part, within the high voltage coil ($L_4$).

5. The sound wave treatment device according to claim 1, wherein the primary coil ($L_1$) is wound on a primary coil former (32), wherein the high voltage coil former (38) coaxially surrounds the primary coil former (32).

6. The sound wave treatment device according to claim 1, wherein the first and/or the second auxiliary coil ($L_2$, $L_3$) are arranged on a ground end face (36), connected to a ground (Gnd), of the transformer (24).

7. The sound wave treatment device according to claim 1, wherein the primary coil ($L_1$) and the first and/or the second auxiliary coil ($L_2$, $L_3$) are wound on a primary coil former (32).

8. The sound wave treatment device according to claim 1, wherein the spacers (48) have a material having a relative permittivity of greater than 3.0 at a frequency of 1.0 kHz and a temperature of 23° C.

9. The sound wave treatment device according to claim 1, wherein the insulating mass (46) has a material having a relative permittivity of greater than 4.0 at a frequency of 1.0 kHz and a temperature of 23° C.

10. The sound wave treatment device according to claim 1, wherein the transformer (24) has a ferrite core (26) having a saturation flux density of at least 200 mT.

11. The sound wave treatment device according to claim 1, wherein the first auxiliary coil ($L_2$) is arranged on a ground end face (36), connected to a ground (Gnd), of the transformer (24).

12. The sound wave treatment device according to claim 10, wherein the primary coil ($L_1$) and the first auxiliary coil ($L_2$) are wound on a primary coil former (32).

* * * * *